United States Patent
Campiche et al.

(10) Patent No.: US 10,328,011 B2
(45) Date of Patent: Jun. 25, 2019

(54) USE OF PROLINE CONTAINING DIPEPTIDES

(71) Applicant: DSM IP ASSETS B.V., Heerlen (NL)

(72) Inventors: Remo Campiche, Kaiseraugst (CH); Dominik Imfeld, Kaiseraugst (CH); Alexandre Rio, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/060,571

(22) PCT Filed: Dec. 9, 2016

(86) PCT No.: PCT/EP2016/080463
§ 371 (c)(1),
(2) Date: Jun. 8, 2018

(87) PCT Pub. No.: WO2017/102588
PCT Pub. Date: Jun. 22, 2017

(65) Prior Publication Data
US 2018/0360722 A1    Dec. 20, 2018

(30) Foreign Application Priority Data

Dec. 16, 2015  (EP) .................................... 15200510
Mar. 10, 2016  (EP) .................................... 16159699

(51) Int. Cl.
*A61K 8/06*    (2006.01)
*A61K 8/55*    (2006.01)
*A61K 8/64*    (2006.01)
*A61Q 19/00*    (2006.01)
*A61Q 19/08*    (2006.01)

(52) U.S. Cl.
CPC ................ *A61K 8/64* (2013.01); *A61K 8/062* (2013.01); *A61K 8/55* (2013.01); *A61Q 19/00* (2013.01); *A61Q 19/007* (2013.01); *A61Q 19/08* (2013.01)

(58) Field of Classification Search
None
See application file for complete search history.

(56) References Cited

U.S. PATENT DOCUMENTS

| 7,964,630 B2 | 6/2011 | Imfeld et al. |
| 2010/0215726 A1 | 8/2010 | Roth |
| 2012/0213845 A1 | 8/2012 | Bernstein |

OTHER PUBLICATIONS

International Search Report for PCT/EP2016/080463 dated Apr. 5, 2017, 4 pages.
Written Opinion of the ISA for PCT/EP2016/080463 dated Apr. 5, 2017, 8 pages.
"Instant Brightening Moisturiser", MINTEL, Nov. 1, 2011, XP002683631, 4 pages.
"Matrikines and Rejuvenation", Sederma, May 4, 2015, XP055249090, 39 pages.

*Primary Examiner* — Brian J Davis
(74) *Attorney, Agent, or Firm* — Nixon & Vanderhye P.C.

(57) ABSTRACT

Proline containing dipeptides are disclosed for up-regulating of genes involved in collagen fiber maturation and thus for revitalizing, strengthening and increasing the integrity of collagen fibers. These proline containing dipeptides are furthermore particularly suitable for improving the skin firmness, texture and elasticity as well as reducing the pore size and increasing skin moisturization.

10 Claims, No Drawings

USE OF PROLINE CONTAINING DIPEPTIDES

This application is the U.S. national phase of International Application No. PCT/EP2016/080463 filed Dec. 9, 2016, which designated the U.S. and claims priority to EP Patent Application No. 15200510.4 filed Dec. 16, 2015 and EP Patent Application No. 16159699.4 filed Mar. 10, 2016, the entire contents of each of which are hereby incorporated by reference.

The present invention relates to a novel use of proline containing dipeptides for upregulating genes involved in collagen fiber maturation and thus for revitalizing, strengthening and increasing the integrity of collagen fibers. These proline containing dipeptides are furthermore particular suitable for improving skin firmness, resiliency, texture and elasticity as well as reducing skin pore size and increasing skin moisturization.

The epidermis and the dermis, which constitutes the two main layers of human skin, have several vital function such as preventing loss of moisture, forming a protective barrier and providing structural support. It is well known, however, that skin aging initiates deep changes at both dermis and epidermis level resulting in a reduced renewal of collagen fiber and a disorganization of the extracellular matrix containing such collagen fibers.

Collagen fibers are the main components of the extracellular matrix of the dermis where they provide structural support. Deterioration of the dermal collagen fiber network due to skin aging thus results in a reduced extracellular matrix network, which in turn leads to several unwanted skin conditions such as uncontrolled water loss, loss of elasticity and firmness as well as increased pore size.

In order to maintain an intact collagen fiber network there is therefore an ongoing need for substances which are capable to up-regulate those genes which are known to be involved in collagen fiber maturation such as ADAMTS2, PLOD3, LOXL and PCOLCE.

Surprisingly, it has been found that certain proline containing dipeptides are capable of upregulating all of the above mentioned genes involved in collagen maturation and are thus particular suitable for improving skin firmness, resiliency, texture and elasticity as well as reducing skin pore size and increasing skin moisturization.

Thus, the first object of the present invention relates to the use of a compound of formula (I)

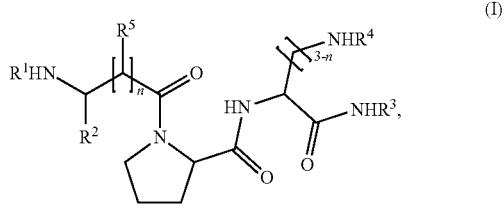

(I)

wherein n represents 0, 1 or 2, $R^1$ and $R^4$—independently of each other—are selected from the group consisting of H, $C_1$-$C_6$alkyl, amidino or tetra-$C_1$-$C_6$-alkylamidinium, $R^2$ is H or $C_1$-$C_6$-alkyl, or $R^1$ and $R^2$ together with the residue to which they are bound form a 5- to 7-membered, saturated ring;

$R^3$ is selected from the group consisting of $C_1$-$C_6$alkyl, ar$C_1$-$C_6$alkyl and heteroaryl$C_1$-$C_6$alkyl; and $R^5$ is H and, when n is 1, also $NH_2$, or $R^5$ and $R^1$ together with the residue to which they are bound form a 5- to 7-membered, saturated ring;

or a cosmetically acceptable salt thereof for revitalizing, strengthening and increasing the integrity of collagen fibers, increasing skin elasticity and/or resiliency, improving skin moisturization and/or skin firmness and/or reducing skin pore size.

In another object, the invention relates to a method to revitalize, strengthen and increase the integrity of collagen fibers as well as to increase skin elasticity and/or resiliency, to improve skin firmness and/or skin moisturization and/or to reduce skin pore size, said method comprises topically administering an effective amount of a cosmetic composition comprising at least one compound of formula (I) to the appropriate skin area of a person in need of such treatment and optionally appreciating the effect.

In a specific embodiment, the invention also relates to the use of a compound of formula (I) with all the preferences and definitions given herein to upregulate genes which are involved in collagen fiber maturation such as in particular ADAMTS2, PLOD3, LOXL and PCOLCE as well as to the to the (medical) use of a compound of formula (I) with all the preferences and definitions given herein for preventing or treating illnesses or conditions connected with reduced ADAMTS2, PLOD3, LOXL and/or PCOLCE activity or capable of being prevented or alleviated by increasing the ADAMTS2, PLOD3, LOXL and PCOLCE activity.

The (total) amount of the at least one compound of formula (I) in the cosmetic composition is preferably selected in the range of 0.5 ppm to 5,000 ppm, preferably in the 2.5 ppm to 250 ppm, most preferably in the range of 25ppm to 100 ppm, based on the total weight of the composition.

The term 'an effective amount' refers to an amount necessary to obtain the physiological effect. The physiological effect may be achieved by one application dose or by repeated applications. The dosage administered may, of course, vary depending upon known factors, such as the physiological characteristics of the particular composition comprising the at least one compound of formula (I) and its mode and route of administration; the age, health and weight of the recipient; the nature and extent of the symptoms; the kind of concurrent treatment; the frequency of treatment; and the effect desired and can be adjusted by a person skilled in the art. Preferably, the amount of the cosmetic composition to be applied to the skin is selected in the range of 0.1 to 3 mg/cm² skin, such as preferably in the range of 0.1 to 2 mg/cm² skin and most preferably in the range of 0.5 to 2 mg/cm² skin. In a preferred embodiment, the cosmetic composition is applied once or twice daily.

The term '$C_1$-$C_6$alky' as used herein refers to unbranched $C_1$-$C_6$alkyl or branched $C_3$-$C_6$alkyl groups such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl groups.

The term 'arC$_1$-C$_6$alky' as used herein refers to a —C$_1$-C$_6$alkyl-aryl wherein the term 'aryl' is e.g. a phenyl, indanyl or naphthyl group.

The term 'heteroarylC$_1$-C$_6$alky' as used herein refers to a —C$_1$-C$_6$alkyl-heteroaryl wherein the term "heteroaryl" refers to a 5- or 6-membered aromatic ring containing one or more heteroatoms, viz., N, O or S; these heteroaromatic rings may be fused to other aromatic systems.

Examples for the 5- to 7-membered, saturated ring, that R$^1$ and R$^2$ or R$^1$ and R$^5$, respectively, may form together with the residue to which they are bound, are pyrrolidinyl, piperidinyl, piperazinyl, morpholinyl, azepinyl, oxazolidinyl, thiazolidinyl and 1,2,3,4- tetrahydroquinolinyl.

It is well understood, that the present invention encompasses the compounds of formula (I) as optically pure isomers such as e.g. as pure enantiomers or stereoisomers as well as mixtures of different isomers such as e.g. as racemates, or mixtures of diastereoisomers.

The term 'or a cosmetically acceptable salt thereof' refers to compounds of formula (I) in the form of an acid addition salt such as in the form of a chloride, an acetate or a trifluoroacetate salt. Alternatively, the salt may be formed by reaction with an alkali or earth alkaline base resulting in the respective alkali or earth alkaline salt such as in particular the respective lithium, sodium, potassium, magnesium or calcium salts.

Most preferred, in all embodiments of the present invention, are the compounds of formula (I) in the form of their acetates or trifluoroacetates. Such salts are easily prepared by a person skilled in the art.

In all embodiments of the present invention R$^1$, R$^4$ and R$^5$ are preferably H.

In all embodiments of the present invention R$^2$ is preferably H and methyl, most preferably H.

In all embodiments of the present invention R$^3$ is preferably arC$_1$-C$_6$alkyl, most preferably benzyl.

In all embodiments of the present invention n is preferably 0 or 1, most preferably 1.

Most preferred in all embodiments of the present invention is a compound of formula (I), wherein R$^1$, R$^2$, R$^4$ and R$^5$ are H, R$^3$ is benzyl and n is 1.

The compounds of formula (I) can be prepared as e.g. disclosed in US 2009/0111731.

Particular advantageous in all embodiments of the present invention is the dipeptide having the sequence H-(beta-Ala)-Pro-Dab-NH-benzyl, in particular as diacetate. This compound is also known as Dipeptide Diaminobutyroyl Benzylamide Diacetate (INCI) [CAS 823202-99-9], and is commercially available as SYN®-AKE from DSM Nutritional products Ltd.

It is well understood that the uses herein, if not stated otherwise, shall in particular refer to a cosmetic, non-therapeutical use intended to beautify the skin, preferably by topical application of a compound according to the present invention to the skin, preferably via a cosmetic composition.

The term 'cosmetic composition' refers to compositions, which are used to treat, care for or improve the appearance of the skin and/or the scalp. Particular advantageous cosmetic compositions are skin care preparations.

The cosmetic compositions according to the invention are preferably intended for topical application, which is to be understood as the external application to keratinous substances, such as in particular the skin.

As the compositions according to the invention are intended for topical application, they comprise a physiologically acceptable medium, that is to say a medium compatible with keratinous substances, such as the skin, mucous membranes, and keratinous fibers. In particular the physiologically acceptable medium is a cosmetically acceptable carrier.

The term 'cosmetically acceptable carrier' as used herein refers to a physiologically acceptable medium which is compatible with keratinous substances. Suitable carriers are well known in the art and are selected based on the end-use application. Preferably, the carriers of the present invention are suitable for application to skin (e.g., sunscreens, creams, milks, lotions, masks, serums, hydrodispersions, foundations, creams, creamgels, or gels etc.). Such carriers are well-known to one of ordinary skill in the art, and can include one or more compatible liquid or solid filler diluent, excipient, additive or vehicle which are suitable for application to skin. The exact amount of carrier will depend upon the level of the compound of formula (I) and any other optional ingredients that one of ordinary skill in the art would classify as distinct from the carrier (e.g., other active components). The compositions of the present invention preferably comprise from about 75% to about 99.999%, more preferably from about 85% to about 99.99%, still more preferably from 90% to about 99%, and most preferably, from about 93% to about 98%, by weight of the composition, of a carrier.

The cosmetic compositions of the present invention can be formulated into a wide variety of product types, including creams, waxes, pastes, lotions, milks, mousses, gels, oils, tonics, and sprays. Preferably the compounds of formula (I) are formulated into lotions, creams, gels, and tonics. These product forms may be used for a number of applications, including, but not limited to, hand and body lotions, facial moisturizers, anti-ageing preparations, make-ups including foundations, and the like. Any additional components required to formulate such products vary with product type and can be routinely chosen by one skilled in the art.

If compositions of the present invention are formulated as an aerosol and applied to the skin as a spray-on product, a propellant is added to the composition.

The cosmetic compositions according to the present invention can be prepared by conventional methods in the art such as e.g. by admixing a compound of formula (I) with all the definitions and preferences given herein with the cosmetically acceptable carrier. The cosmetic compositions of the invention (including the carrier) may comprise further conventional cosmetic adjuvants and additives, such as preservatives/antioxidants, fatty substances/oils, water, organic solvents, silicones, thickeners, softeners, emulsifiers, antifoaming agents, aesthetic components such as fragrances, surfactants, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the cosmetic compositions according to the invention may also comprise further cosmetically active ingredients conventionally used in cosmetic compositions. Exemplary active ingredients encompass skin lightening agents; UV-filters, agents for the treatment of hyperpigmentation; agents for the prevention or reduction of inflammation; firming, moisturizing, soothing, and/or energizing agents as well as agents to improve elasticity and skin barrier.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the cosmetic excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

The cosmetic compositions according to the present invention may be in the form of a suspension or dispersion in solvents or fatty substances, or alternatively in the form of an emulsion or micro emulsion (in particular of oil-in-water (O/W) or water-in-oil (W/O) type, silicone-in-water (Si/W) or water-in-silicone (W/Si) type, PIT-emulsion, multiple emulsion (e.g. oil-in-water-in oil (O/W/O) or water-in-oil-in-water (W/O/W) type), pickering emulsion, hydrogel, alcoholic gel, lipogel, one- or multiphase solution or vesicular dispersion or other usual forms, which can also be applied by pens, as masks or as sprays.

If the cosmetic composition is an emulsion, such as in particular an O/W, W/O, Si/W, W/Si, O/W/O, W/O/W multiple or a pickering emulsion, then the amount of the oily phase present in such cosmetic emulsions is preferably at least 10 wt.-%, such as in the range of 10 to 60 wt.-%, preferably in the range of 15 to 50 wt.-%, most preferably in the range of 15 to 40 wt.-%, based on the total weight of the cosmetic composition.

In one embodiment, the cosmetic compositions according to the present invention are advantageously in the form of an oil-in-water (O/W) emulsion comprising an oily phase dispersed in an aqueous phase in the presence of an O/W emulsifier. The preparation of such O/W emulsions is well known to a person skilled in the art.

If the cosmetic composition according to the invention is an O/W emulsion, then it contains advantageously at least one O/W- or Si/W-emulsifier selected from the list of, glyceryl stearate citrate, glyceryl stearate SE (self-emulsifying), stearic acid, salts of stearic acid, polyglyceryl-3-methylglycosedistearate. Further suitable emulsifiers are phosphate esters and the salts thereof such as cetyl phosphate (e.g. as Amphisol® A from DSM Nutritional Products Ltd.), diethanolamine cetyl phosphate (e.g. as Amphisol® DEA from DSM Nutritional Products Ltd.), potassium cetyl phosphate (e.g. as Amphisol® K from DSM Nutritional Products Ltd.), sodium cetearylsulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, cetearyl glucoside, lauryl glucoside, decyl glucoside, sodium stearoyl glutamate, sucrose polystearate and hydrated polyisobutene. Furthermore, one or more synthetic polymers may be used as an emulsifier. For example, PVP eicosene copolymer, acrylates/C10-30 alkyl acrylate crosspolymer, and mixtures thereof.

The at least one O/W, respectively Si/W emulsifier is preferably used in an amount of 0.5 to 10 wt. %, in particular in the range of 0.5 to 6 wt.-%, such as more in particular in the range of 0.5 to 5 wt.-%, such as most in particular in the range of 1 to 4 wt.-%, based on the total weight of the cosmetic composition.

Particular suitable O/W emulsifiers to be used in the cosmetic compositions according to the invention encompass phosphate ester emulsifiers such as advantageously 8-10 alkyl ethyl phosphate, C9-15 alkyl phosphate, ceteareth-2 phosphate, ceteareth-5 phosphate, ceteth-8 phosphate, ceteth-10 phosphate, cetyl phosphate, C6-10 pareth-4 phosphate, C12-15 pareth-2 phosphate, C12-15 pareth-3 phosphate, DEA-ceteareth-2 phosphate, DEA-cetyl phosphate, DEA-oleth-3 phosphate, potassium cetyl phosphate, deceth-4 phosphate, deceth-6 phosphate and trilaureth-4 phosphate.

Particular suitable O/W emulsifier to be used in the cosmetic compositions according to the invention are the cetyl phosphates such as preferably potassium cetyl phosphate which is e.g. commercially available as Amphisol® K at DSM Nutritional Products Ltd Kaiseraugst.

Another particular suitable class of O/W emulsifiers are non-ionic self-emulsifying systems derived from olive oil e.g. known as (INCI Name) cetearyl olivate and sorbitan olivate (chemical composition: sorbitan ester and cetearyl ester of olive oil fatty acids) sold under the tradename OLIVEM 1000.

In one particular embodiment, the invention relates to cosmetic compositions with all the definitions and preferences given herein in the form of O/W emulsions comprising an oily phase dispersed in an aqueous phase in the presence of an O/W emulsifier wherein the O/W emulsifier is potassium cetyl phosphate. The amount of oily phase in such O/W emulsions is preferably at least 10 wt.-%, more preferably in the range of 10 to 60 wt.-%, most preferably in the range of 15 to 50 wt.-%, such as in the range of 15 to 40 wt.-%.

The cosmetic compositions according to the invention in general have a pH in the range of 3 to 10, preferably a pH in the range of 4 to 8 and most preferably a pH in the range of 4 to 7.5. The pH can easily be adjusted as desired with suitable acids, such as e.g. citric acid, or bases, such as sodium hydroxide (e.g. as aqueous solution), triethanolamine (TEA Care), Tromethamine (Trizma Base) and Aminomethyl Propanol (AMP-Ultra PC 2000), according to standard methods in the art.

The following examples are provided to further illustrate the compositions and effects of the present invention. These examples are illustrative only and are not intended to limit the scope of the invention in any way.

EXPERIMENTAL PART

1. Genes

PLOD3: The enzyme catalyzes the hydroxylation of lysyl residues in collagen-like peptides. The resultant hydroxylysyl groups are attachment sites for carbohydrates in collagen and thus are critical for the stability of intermolecular crosslinks.

LOXL2: This gene encodes a member of the lysyl oxidase gene family that catalyses the first step in the formation of crosslinks in collagens.

ADAMTS2 is responsible for processing several types of procollagen proteins. Specifically, this enzyme clips a short chain of amino acids off one end of the procollagen. This clipping step is necessary for collagen molecules to function normally and assemble into fibrils outside cells.

PCOLCE: This gene encodes a glycoprotein which binds and drives the enzymatic cleavage of type I procollagen upon secretion from the cell, to yield the mature triple helical, highly structured fibrils.

2. Material & Methods

Gene-Expression Analysis

Normal human dermal fibroblasts at passage 7 from a 63 year old female donor were cultured in DMEM with L-glutamine 2 mM, Penicillin 50 U/ml-Streptomycin 50 ug/ml and 10% FCS in a 5% $CO_2$ atmosphere at 37° C. After equilibration of cell in 1% FCS for 24 hrs the respective peptides H-(beta-Ala)-Pro-Dab-NH-benzyl [CAS 823202-99-9], respectively N-palmitoyl-Gly-His-Lys [147732-56-7]/N-palmitoyl-Gly-Gln-Pro-Arg [221227-$C_5$-0] (2:1) diluted in growth medium to a concentration of 0.01% were added and the cells were incubated for an additional 24 hrs. At the end of incubation cells were washed in PBS and immediately frozen at −80° C. Total RNA was extracted using NucleoSpin RNA Plus kit (Macherey-Nagel) according to supplier's instructions. cDNA was synthesized by reverse transcription of total RNA using Transcriptor Reverse Transcriptase (Roche). PCR was performed on a LightCycler device (Roche Molecular Systems Inc.) according to manufacturer's instructions. Raw data were analyzed using Microsoft Excel.

3. Clinical Study

A double blind parallel group study was performed with Caucasian female volunteers aged 40-55. 30 volunteers (mean age 46+/−1 year) received a placebo formulation and 29 volunteers (mean age 48+/−1 year) received a verum formulation containing SYN®-AKE. The placebo respectively verum formulation was applied twice daily for 28 days to face. At the end of the study pictures were taken for computational analysis of pores: 1 photograph of the entire face (90°) was taken with Newtone® Color face for the pore size analysis. Furthermore a questionnaire was filled out by the volunteers.

TABLE 1

Placebo/Verum formulation

| Phase | Ingredients | INCI Name | A Placebo | B Verum |
|---|---|---|---|---|
| A | AMPHISOL ® K | Potassium cetyl phosphate | 1.00 | 1.00 |
| | Ecorol 16/98P | Cetyl alcohol | 3.00 | 3.00 |
| | Cutina CP | Cetyl palmitate | 1.50 | 1.50 |
| | Eutanol G | Octyldodecanol | 3.00 | 3.00 |
| B | Pemulen TR-1 | Acrylates/C10-30 alkyl acrylate crosspolymer | 0.10 | 0.10 |
| C | 1,3-Butylenglycol | Butylene glycol | 3.00 | 3.00 |
| | Water dem. | Aqua | Ad 100 | Ad 100 |
| D | Dow Corning 345 Fluid | Cyclopentasiloxane, cyclohexasiloxane | 2.50 | 2.50 |
| E | Natriumhydroxid 30% soln. | Aqua, sodium hydroxide | 0.09 | 0.09 |
| F | SYN ®-AKE | Dipeptide Diaminobutyroyl Benzylamide Diacetate, Glycerin, Aqua | 0 | 4.00 |
| G | Euxyl PE 9010 | Phenoxyethanol, ethylhexylglycerine | 1.00 | 1.00 |
| G | Frag 49424902 Chloe | Perfume | 0.05 | 0.05 |

4. Results 4.1 Gene-Expression Study

TABLE 2

Results of the gene expression assay

| Gene: | Time-point | H-(β-Ala)-Pro-Dab-NH-benzyl | N-palmitoyl-Gly-His-Lys//N-palmitoyl-Gly-Gln-Pro-Arg * |
|---|---|---|---|
| PLOD3 | 24 hrs | 299% | 163% |
| LOXL2 | 24 hrs | 237% | 292% |
| PCOLCE | 24 hrs | 137% | 94% |
| ADAMTS2 | 24 hrs | 151% | 105% |

* Reference peptide (MATRIXYL ™ 3000)

As can be retrieved from table 1, H-(beta-Ala)-Pro-Dab-NH-benzyl) significantly upregulates genes involved in collagen fiber maturation, whereas Matrixyl3000 only upregulates LOXL2 and much less PLOD3.

4.2 Pores on Forehead

TABLE 3

Results of the computational analysis of the pores

| Number of Pores D0 to D28 | |
|---|---|
| Placebo | +3.2% |
| SYN ®-AKE | −0.8% |
| Conspicuous surface of each pore D0 to D28 | |
| Placebo | −3.2% |
| SYN ®-AKE | −4.4% |
| Conspicuous surface of all pores D0 to D28 | |
| Placebo | +1.5% |
| SYN ®-AKE | −2.7% |
| Conspicuous volume D0 to D28 | |
| Placebo | +3.8% |
| SYN ®-AKE | −1.3% |

As can be retrieved from table 2, the pore size was significantly reduced by the treatment with the composition comprising a compound of formula (I) according to the invention.

4.3 Results from Questionnaire

TABLE 4

Results from the questionnaire

| Moisturized Skin | Agree |
|---|---|
| Placebo | 76% |
| SYN ®-AKE | 93% |
| Pore Size Reduction | Agree |
| Placebo | 60% |
| SYN ®-AKE | 69% |

As can be retrieved from table 4, a significant moisturizing effect as well as a perceivable pore size reduction was observed by the volunteers.

The invention claimed is:

1. A method of treating skin to up-regulate genes involved in collagen fiber maturation, wherein the method comprises topically administering to an appropriate skin area of a person in need of treatment an effective amount of a cosmetic composition comprising at least one compound of formula (I) or a cosmetically acceptable salt thereof:

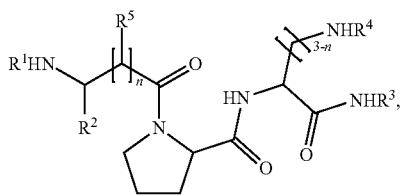

wherein n represents 0, 1 or 2, $R^1$ and $R^4$ —independently of each other —are selected from the group consisting of H, $C_1$-$C_6$alkyl, amidino or tetra-$C_1$-$C_6$-alkylamidinium, $R^2$ is H or $C_1$-$C_6$-alkyl, or $R^1$ and $R^2$ together with the residue to which they are bound form a 5- to 7-membered, saturated ring, $R^3$ is selected from the group consisting of $C_1$-$C_6$alkyl, ar$C_1$-$C_6$alkyl and heteroaryl$C_1$-$C_6$alkyl, and $R^5$ is H or, when n is 1, also $NH_2$, or $R^5$ and $R^1$ together with the residue to which they are bound form a 5- to 7-membered, saturated ring.

2. The method according to claim 1, wherein the amount of the at least one compound of formula (I) or cosmetically acceptable salt thereof in the cosmetic composition is in a range of 0.5 ppm to 5000 ppm, based on the total weight of the cosmetic composition.

3. The method according to claim 1, wherein the method comprises topically administering to the skin an amount of the cosmetic composition in a range of 0.1 to 3 mg/ $cm^2$ of skin.

4. The method according to claim 1, wherein the method comprises applying the cosmetic composition to the skin once or twice daily.

5. The method according to claim 1, wherein the composition is an oil/water (O/W) emulsion comprising an oily phase dispersed in an aqueous phase in the presence of an O/W emulsifier.

6. The method according to claim 5, wherein the O/W emulsifier is a cetyl phosphate.

7. The method according to claim 2, wherein the amount of the at least one compound of formula (I) or cosmetically acceptable salt thereof in the cosmetic composition is in a range of 2.5 ppm to 250 ppm, based on the total weight of the cosmetic composition.

8. The method according to claim 2, wherein the amount of the at least one compound of formula (I) or cosmetically acceptable salt thereof in the cosmetic composition is in a range of 25 ppm to 100 ppm, based on the total weight of the cosmetic composition.

9. The method according to claim 3, wherein the method comprises topically administering to the skin an amount of the cosmetic composition in the range of 0.1 to 2 mg/ $cm^2$ of skin.

10. The method according to claim 3, wherein the method comprises topically administering to the skin an amount of the cosmetic composition in the range of 0.5 to 2 mg/ $cm^2$ of skin.

* * * * *